US00PP18412P2

(12) United States Plant Patent
Korlipara

(10) Patent No.: US PP18,412 P2
(45) Date of Patent: Jan. 8, 2008

(54) ***ECHINACEA PURPUREA* PLANT NAMED 'MARS'**

(50) Latin Name: *Echinacea purpurea*
Varietal Denomination: Mars

(75) Inventor: Harini Korlipara, Canby, OR (US)

(73) Assignee: Terra Nova Nurseries, LLP, Canby, OR (US)

( * ) Notice: Subject to any disclaimer, the term of this patent is extended or adjusted under 35 U.S.C. 154(b) by 0 days.

(21) Appl. No.: 11/473,493

(22) Filed: Jun. 23, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct *Echinacea purpurea* plant named 'Mars' characterized by red purple, medium-sized flowers; large, ball-like disc; lime green centers when disc florets are unopened; well branched habit; lovely fragrance; and good vigor.

1 Drawing Sheet

Botanical denomination: *Echinacea purpurea.*
Variety designation: 'Mars'.

The present invention relates to a new and distinct cultivar of *Echinacea purpurea* and given the cultivar name 'Mars'. *Echinacea* is in the family Asteraceae. This new cultivar originated as a seedling from an open pollinated cross between *Echinacea* 'Ruby Giant', an unpatented plant, as the seed parent and an unknown pollen parent.

This new *Echinacea purpurea* cultivar is distinguished by:

1. Red purple, medium-sized flowers.
2. Large, ball-like disc.
3. Lime green centers when disc florets are unopened.
4. Well branched habit.
5. Lovely fragrance.
6. Good vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows one year old *Echinacea purpurea* 'Mars' growing in the ground in the field in the summer in Canby, Oreg.

DETAILED PLANT DESCRIPTION

The following is a detailed description of the new *Echinacea purpurea* cultivar based on observations of a one-year-old specimen growing in the ground in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—45 cm wide and 72 cm tall to top of inflorescence.
- *Form.*—Basal clump.
- *Vigor.*—Excellent.
- *Roots.*—Fibrous, with many downward growing and few laterals, ivory in color, Yellow White 158D, roots develop easily from crown divisions.

Stem:
- *Type.*—Ascending.
- *Size.*—69 cm tall to terminal flower and 9 mm wide.
- *Internode length.*—5 to 10 cm.
- *Surface texture.*—Strigose.
- *Color.*—Yellow Green 152A mottled with Greyed Orange 175A.

Leaves, basal and cauline:
- *Type.*—Simple.
- *Shape.*—Ovate.
- *Arrangement.*—Alternate.
- *Blade size.*—Grows to 26 cm long and 10 cm wide.
- *Margins.*—Finely serrate.
- *Apex.*—Acuminate.
- *Base.*—Attenuate, continuing down petiole.
- *Surface texture.*—Strigose.
- *Venation.*—Pinnate.
- *Color.*—Topside — deep Green, Between Green 139A and Yellow Green 147A with the vein Yellow Green 145B. Bottom side — Yellow Green 147B with the veins Yellow Green 147C.
- *Petiole size.*—15 cm if basal leaf, 7 cm if cauline leaf and 5 mm wide on both.
- *Petiole surface texture.*—Strigose.
- *Petiole color.*—Yellow Green 147B on backside and Greyed Purple 187A on the top.

Inflorescence:

*Type.*—Long stalked terminal heads.

*Peduncle description.*—Grows to 26 cm where leafless, with diameter growing to 6 mm near the inflorescence, strigose, branched, with three to five flowering stems, Yellow Green 152A mottled with Greyed Orange 175A.

*Size.*—9 cm wide and 6 cm deep as disc enlarges.

*Bloom time.*—Summer until frost in Canby, Oreg.

*Immature inflorescence.*—7 cm wide and 2.5 cm deep, ray florets held slightly upright and colored Red Purple 59D with greenish tinge, Greyed Yellow 160D. The disc is Greyed Red 178A on the outer edge with the center Yellow Green 144B.

Florets:

*Type.*—Zygomorphic.

*Form.*—Ray florets held horizontally on young inflorescences, when the discs are mature they tilt down at a 20 degree angle; mature discs have a strawberry shape.

*Ray florets.*—Average 34 in number, without pistil or stamen, oblanceolate with the tip two toothed, entire margins, 4 cm long, 9 mm wide, glabrous on both sides.

*Disc.*—Convex becoming conic, 3.3 cm to 5 cm wide and becoming 4 cm deep with maturity.

*Disc florets.*—About 400 in number, 12 mm long, Yellow Green 144B, 5 lobed, each floret with one persistent, very still bract, 13 mm long, which gives the disc color, with pistil and stamen. Pistil — 1 in number, 12 mm long, with an extruding, 2-branched stigma, Greyed Purple 187A. Stamen — 5 in number, each 7 mm long, extruding from corolla, anthers 2.5 mm long and Brown 200A, pollen Yellow Orange 13C.

*Color.*—Ray florets, topside — Red Purple 67A to 71B but brighter ray florets, bottom side — Red Purple 63A to Greyed Purple 186A disc — Yellow Green 144A when in bud, changing to deep orange, Greyed Red 179A then mature to Greyed Orange 170A.

*Phyllaries.*—In four leafy series, lobes lanceolate in shape, reflexed, strigose, area 3.7 cm wide, grow to 7 mm long and 2.5 mm wide, Yellow Green 147B.

*Bloom period.*—July through October in Canby, Oreg.

*Fragrance.*—Lovely, strong.

Seed: Average 3 seeds/head.

*Description.*—4.5 mm long and 2 mm wide, oval, tan, Grey Brown 199D.

*Fertility.*—Low.

Disease and pests: *Echinacea* are susceptible to leaf miners, powdery mildew, bacterial spots, and gray mold. None of these have been observed on plants grown under commercial conditions in Canby, Oreg.

COMPARISONS TO SIMILAR *ECHINACEA*

Compared to *Echinacea purpurea* 'Ruby Giant', an unpatented plant, the new variety has smaller, brighter red purple flowers, more flowers, and fewer petal layers. The overall plant habit is smaller. The petals of this new variety reflex back slightly with maturity.

Compared to *Echinacea purpurea* 'Green Eyes' (U.S. Plant Pat. No. 17,172) the flowers of this new cultivar are smaller, brighter colored and the petal reflex back slightly with maturity. The disc of the new variety become much larger with maturity.

I claim:

1. A new and distinct *Echinacea purpurea* plant named 'Mars' as herein illustrated and described.

* * * * *

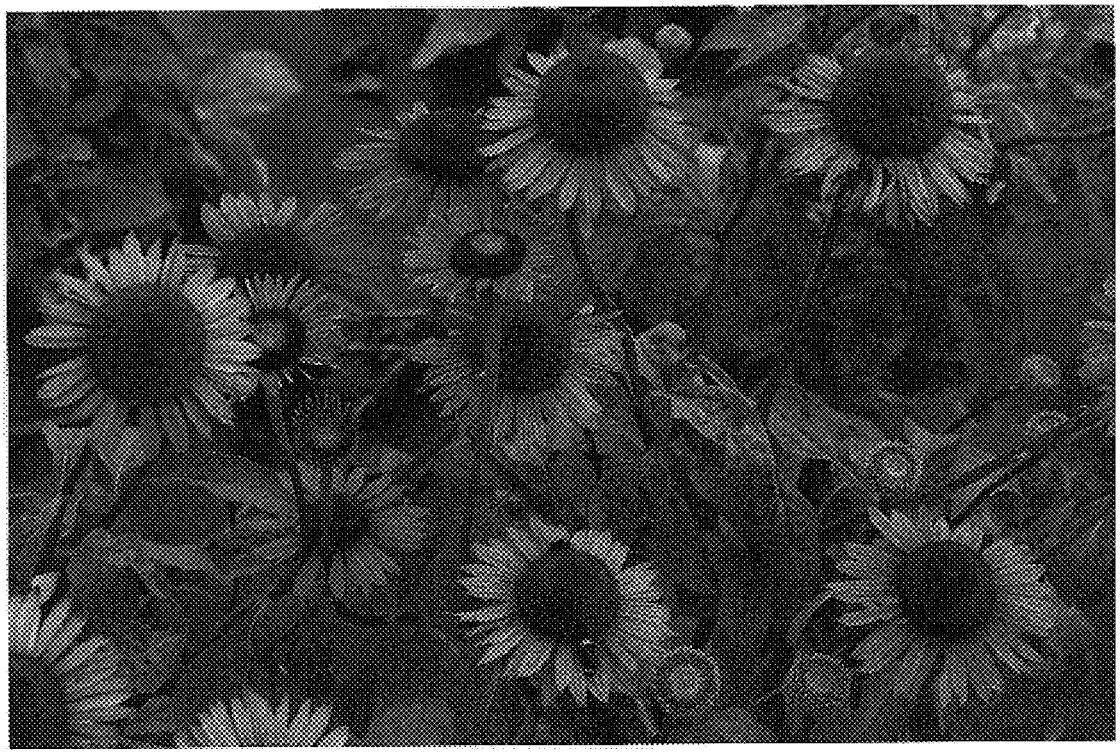

UNITED STATES PATENT AND TRADEMARK OFFICE

CERTIFICATE OF CORRECTION

PATENT NO. : PP 18,412 P2
APPLICATION NO. : 11/473493
DATED : January 8, 2008
INVENTOR(S) : Harini Korlipara It is certified that error appears in the above-identified patent and that said Letters Patent is hereby corrected as shown below:

On the Title Page:

Item (73) Assignee: "Terra Nova Nurseries, LLP" should be --Terra Nova Nurseries, Inc.--

In the Specification:

Column 3, line 29, "very still bract" should be --very stiff bract--.

Signed and Sealed this

Nineteenth Day of August, 2008

JON W. DUDAS
*Director of the United States Patent and Trademark Office*